(12) United States Patent
Vargas Fonseca (10) Patent No.: US 10,352,473 B2
(45) Date of Patent: Jul. 16, 2019

(54) MEMBRANE VALVE FOR CONTROLLING FLOW AND PRESSURE RELIEF

(71) Applicant: ZAMMI INSTRUMENTAL LTDA, Duque de Caxias (BR)

(72) Inventor: Luiz Henrique Vargas Fonseca, Duque de Caxias (BR)

(73) Assignee: ZAMMI INSTRUMENTAL LTDA, Duque de Caxias (BR)

( * ) Notice: Subject to any disclaimer, the term of this patent is extended or adjusted under 35 U.S.C. 154(b) by 0 days.

(21) Appl. No.: 15/534,788

(22) PCT Filed: Dec. 11, 2014

(86) PCT No.: PCT/BR2014/050039
§ 371 (c)(1),
(2) Date: Jun. 9, 2017

(87) PCT Pub. No.: WO2016/090438
PCT Pub. Date: Jun. 16, 2016

(65) Prior Publication Data
US 2017/0350529 A1    Dec. 7, 2017

(51) Int. Cl.
*F16K 7/12* (2006.01)
*A61M 39/22* (2006.01)
*F16K 17/16* (2006.01)
*F16K 31/128* (2006.01)

(52) U.S. Cl.
CPC ........... *F16K 31/128* (2013.01); *A61M 39/22* (2013.01); *F16K 7/12* (2013.01); *F16K 17/16* (2013.01)

(58) Field of Classification Search
USPC .................................................. 251/4, 5, 7
See application file for complete search history.

(56) References Cited

U.S. PATENT DOCUMENTS

| | | | | |
|---|---|---|---|---|
| 3,469,582 A | * | 9/1969 | Jackson | A61M 1/0043 137/510 |
| 3,552,712 A | * | 1/1971 | Whitlock | F16K 7/07 251/5 |
| 3,885,769 A | * | 5/1975 | Morrison | F16K 7/07 222/504 |
| 4,111,391 A | * | 9/1978 | Pilolla | F16K 7/07 251/5 |

(Continued)

FOREIGN PATENT DOCUMENTS

EP    1057460 A1    12/2000

OTHER PUBLICATIONS

International Search Report issued in PCT/BR2014/050039 dated Aug. 6, 2015 (2 pages).

(Continued)

*Primary Examiner* — Robert K Arundale
*Assistant Examiner* — Daphne M Barry
(74) *Attorney, Agent, or Firm* — Osha Liang LLP (57) ABSTRACT

A membrane valve for controlling flow and pressure relief has a format following the anatomy and the action mechanism of a sphincter, in order not to have restriction points to the fluid flow. The valve includes a body provided with terminal sections provided with ends and, internally, a folded membrane which opens and closes according to the flow and/or pressure exerted therein, directly or indirectly, locally or remotely.

9 Claims, 5 Drawing Sheets

(56) References Cited

U.S. PATENT DOCUMENTS

| | | | | |
|---|---|---|---|---|
| 4,268,005 A | * | 5/1981 | Raftis | F16K 7/07 251/5 |
| 4,303,100 A | * | 12/1981 | Kalb | E21B 21/106 137/853 |
| 4,811,758 A | * | 3/1989 | Piper | E21B 21/106 137/844 |
| 4,969,513 A | * | 11/1990 | Barrus | E21B 21/106 137/493 |
| 5,161,773 A | * | 11/1992 | Tower | A61M 39/0613 251/5 |
| 5,186,431 A | * | 2/1993 | Tamari | A61M 1/3621 251/5 |
| 5,205,325 A | * | 4/1993 | Piper | E21B 21/10 137/844 |
| 5,535,983 A | * | 7/1996 | Hohermuth | F16K 7/07 251/4 |
| 5,549,793 A | * | 8/1996 | Hellstrom | D21F 1/08 162/258 |
| 7,255,012 B2 | | 8/2007 | Hedtke | |
| 2006/0178731 A1 | * | 8/2006 | Tower | A61F 2/2412 623/1.24 |
| 2015/0267822 A1 | * | 9/2015 | Nissen | F16K 7/07 251/5 |

OTHER PUBLICATIONS

Written Opinion of the International Searching Authority issued in PCT/BR2014/050039 dated Aug. 6, 2015 (3 pages).

\* cited by examiner

FIGURE 13

MEMBRANE VALVE FOR CONTROLLING FLOW AND PRESSURE RELIEF

FIELD

The present application refers to a conception of membrane valve for controlling flow and pressure relief, which has a format following the anatomy and the physiologic mechanism of a sphincter action, in order not to have restriction points to the fluid flow.

Valves are devices by which the hydraulic (or gaseous) systems are controlled, serving generally to direct the flow, provide blocks, control the flow rate or pressure intensity. Valves may be classified regarding the manner they are operated or regarding its function. Regarding the function, valves may be classified as flow rate control valve, direction control valve or pressure control valve.

Flow rate controller valves, which are of several types, function regulating the flow rate of a pumping. It is known that the speed is function of the flow rate and of the section where the flow occurs. Then, it may do the flow rate control modifying the section where the fluid passes, through a flow rate controller valve.

These valves are classified, generally, as:

a. Non-compensated flow control valves, which are the simplest valves that control flow through a throttling or restriction. The amount of flow passing through a hole and the loss of charge therein are directly related so that if the pressure increases, the flow in the valve increases;

b. Compensated flow control valves. They keep the flow rate value independent of the pressure variations in the circuit and, like the non-compensated units, have a hole (or throttling) to adjust the flow rate. The control can be automatic or manual, this being remote or local. The control valve opens and closes the internal passage of the fluid in accordance with a control signal. When the control signal comes from a controller, automatic control of the valve is performed. When the control signal is generated manually by the process operator, through a manual control station, remote manual control is performed. Also, the control can be done continuously or on-off. In continuous or analog mode, the valve can assume, steadily, infinite positions between fully closed and fully open. In digital or "on-off" mode, the valve only comes in two discrete positions: either fully closed or fully open. Such control can be performed by manual keys, keys controlled by pressure (pressure switch), temperature (thermostat), level, flow rate or simpler controllers. The control signal arriving to the valve actuator may be pneumatic or electronic.

BACKGROUND

The control valve with pneumatic actuator is the final control element of the absolute majority of the flow meshes. Even with the increasingly intensive and extensive use of electronic instrumentation, the valve with pneumatic actuator is still the most applied, simpler, more reliable, economical and efficient final element than the valve with electronic actuator, (Ribeiro, 1999).

The pressure control valve is a device having as function to relief the pressure exceeded of a system, either be pipes that transport or store a liquid or a gas under high pressures. The objective of installing a security valve is to protect the system from excessive pressure effects, where there is risk of damaging the system, risk of explosions and life threatening. This protection occurs when a valve is able to discharge a certain flow rate enough to reduce the pressure of a system to a certain level of safety.

It is a device very widely applied in the industry in general, however there is no model on the market specifically designed for application in blood flow control, i.e., it keeps these characteristics and is free from aggression to blood.

Several advisory devices used in extracorporeal circulation (CEC) require a component with this protection function. In CEC, blood is pumped at flows greater than 5 liters per minute. These flows generate high pressures, being able to exceed 300 mmHg, which generates risks of damages to devices such as hemoconcentrators and hemofilters. The hemoconcentrator is a device used in CEC with the function of removing blood liquids, being formed by a bundle of hollow and microporous fibers with walls of microscopic thickness. For example, polysulfone fiber has a thickness of 30 μm and has a low-pressure tolerance. Once the pressure tolerance threshold is exceeded, the fiber may rupture and leak the blood in its interior.

Thus, in order to design a valve model that could provide protection to the hemoconcentrator and, at the same time, would not be aggressive to the blood elements noted from the blood, notably for CEC application, the membrane valve for controlling flow and pressure relief was developed.

DETAILED DESCRIPTION

The membrane valve for controlling flow and pressure relief according to the present application has internal format similar to a sphincter, notably to the pyloric valve, which is one of the most important sphincters of the digestive tract.

Sphincter is a component of the animal anatomy formed by muscular structures of concentric circular fibers arranged ringed that serves to control the amplitude degree and the inlet or outlet flow of a determined hole in a segment of pot, channel or tube. There are at least distinct 43 sphincters in the human body, some of them in microscopic size, such as the pre-capillary sphincters of the blood microcirculation. The pre-capillary sphincters work regulating the blood flow in the capillary network according to the need of the tissue irrigated by the capillary network.

The description as follows exposed will refer to the schematic figures attached, which do not serve to limit the scope and the reach of the valve of the present disclosure. In some of these figures, certain elements would not be identified numerically to ease and provide a clear understanding of its structure, as well as of examples of circuits and devices in which said valve may be applied to, performing different functions.

Thus, according to the FIGS. 1(a)-(f), the membrane valve (1) for controlling flow and pressure relief in accordance with embodiments described herein comprises a body (2) in a circular general format, provided with terminal sections (3, 4) of greater diameter which are provided with ends (5, 6) for connecting in installations of use, such as hydraulic circuits or blood circuits and other devices. In these figures, it is noted that said valve (1) comprises internally a folded membrane (7), i.e., provided with internal folds (7a, 7b, 7c, etc.), which is generally made in flexible material. Generally, the membrane valve for controlling flow and pressure relief according to the present disclosure comprises at least three folding or internal folds (7a, 7b, 7c), but it may have, depending on the project for specific use, more than three folding.

Thereby structured, said folded membrane (7) is assembled inside the valve body (1), in order to form two distinct enclosures, one inner enclosure (8) to said folded membrane (3), like a flow line segment, and other enclosure (9) forming another space between said membrane (7) and the inner wall of the body (2), composing one type of air chamber. It must be noted that said membrane (7) is tied and fixed in the ends (3, 4) hermetically to avoid any communication between the enclosures (8, 9) inside the body (2).

Figure 1:
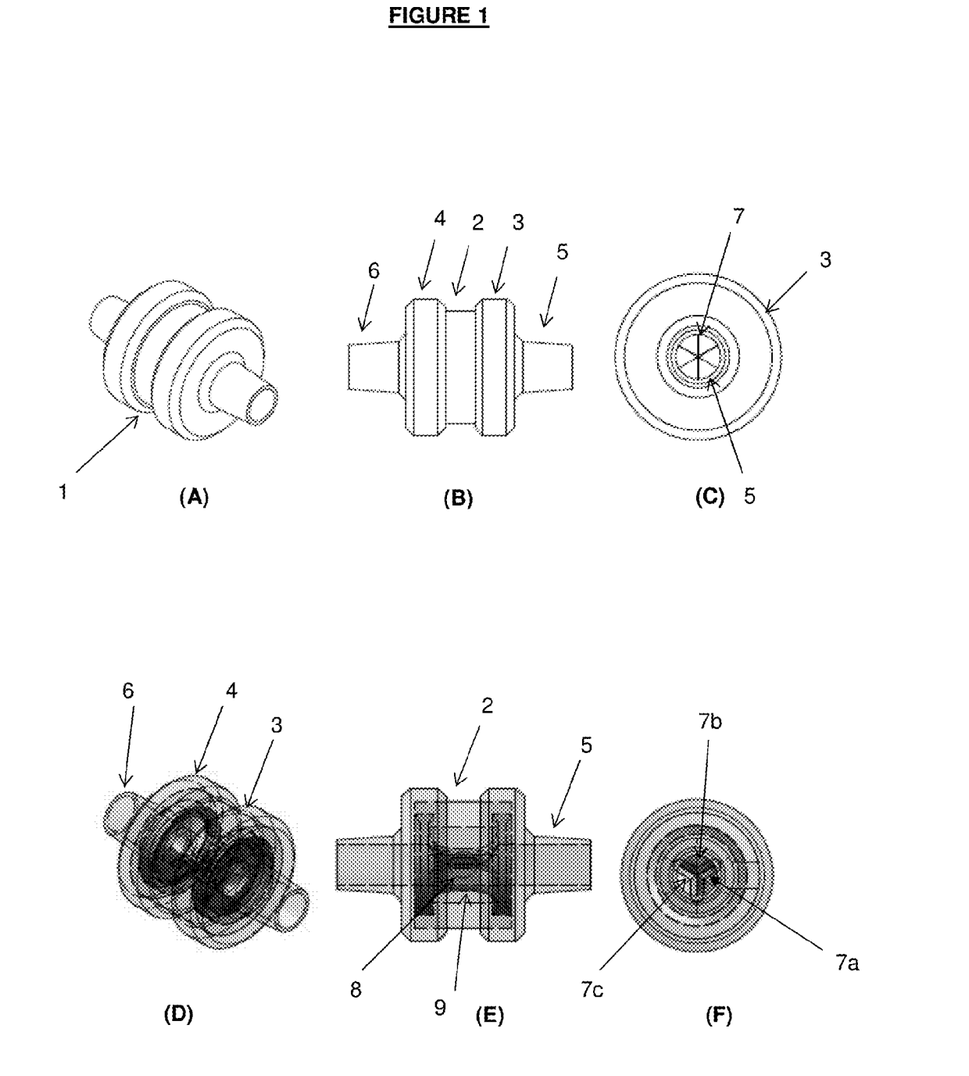
FIGS. 1A-1F show a membrane valve for controlling flow and pressure relief in accordance with embodiments disclosed herein.
Figure 2:
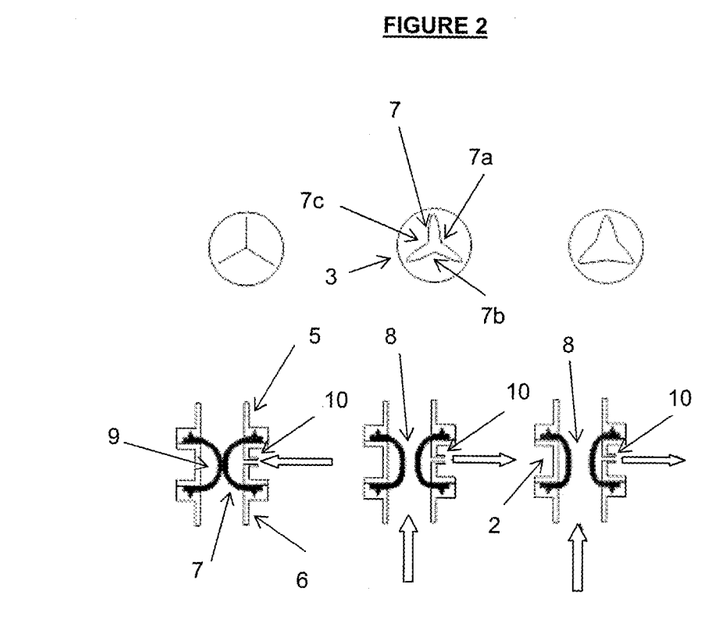
FIG. 2 shows a membrane valve for controlling flow and pressure relief having an outer connector or control door in accordance with embodiments disclosed herein.

The FIG. 2 illustrates the valve (1) according to the present disclosure, varying having an outer connector or control door (10) for acting directly in said enclosure (9) involving axially the enclosure (8) of the membrane (7). Said enclosure (9) fits in its interior a gas or liquid known volume that is fed or removed through an acting element (not shown) installed in said control door (10) in order to allow a pneumatic or hydraulic control of opening or closing the valve (1), either directly or remotely. The arrows illustrate the flow path of the fluid of interest to be controlled, as well as the forms of acting over the content of the illustrated enclosure (9).

As illustrated, the membrane valve (1) for controlling flow and pressure relief in accordance with embodiments disclosed herein has an anatomic format, imitating the anatomy and the action mechanism of a pre-capillary sphincter, allowing to act with the same function without producing greater aggression than the aggression degree imposed by the pre-capillary sphincter. Therefore, if produced in biocompatible material, it may be used in a blood circuit.

The membrane valve (1) for controlling flow and pressure relief in accordance with embodiments disclosed herein does not have restriction points to the flow. In addition, as the membrane (7) is made in flexible material, it allows adjustments in its format if some particle, or solid material, passes by its interior. This possibility may be examined by the illustration of the FIG. 3 showing in succession, configuration of the membrane (7) opening since a position totally closed (a) until a position totally open (f).

Figure 3:
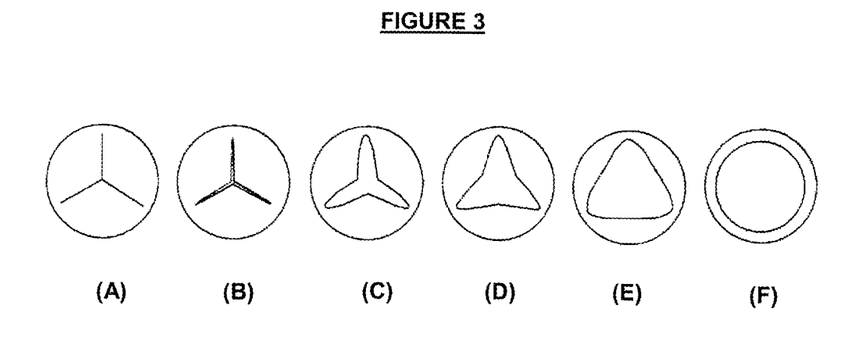
FIGS. 3A-3F show, in succession, a configuration of the membrane opening from a totally closed position (A) to a totally open position (F) in accordance with embodiments disclosed herein.

Considering as base the configurations explained in the FIG. 3 and acting as relief valve, when dully pressurized such that it is normally closed (a) until a determined pressure, if a pressure succeeds greater than the determined one in the flow line, it will open in a position (b-f) allowing the volume exhaust for pressure normalization in the line. The pressure inside the enclosure (9) increases as the flow or the pressure in the inlet line. This causes the membrane valve (1) according to the present disclosure to behave as a variable resistance, reducing with the flow and the pressure. This capability may be used to limit the flow in a line, or for automatic regulation of flow and pressure in one line, once, in low flow; the resistance is high, thus increasing the pressure in the line. However, as the flow increases, the pressure also increases, opening the valve and, thus, reducing the resistance and the pressure in the line.

Some of the several applications and uses of the membrane valve for controlling flow and pressure relief of the present application will be described in the following, but without any intention to restrict its reach and inventive scope.

Tube Segment:

Other functionality of the membrane valve for controlling flow and pressure relief in accordance with embodiments disclosed herein occurs when totally open, such as illustrated in the FIG. 3(f). In this case, the membrane valve (1) behaves as a tube segment, with the same diameter of the inlet connector (5, 6), allowing the free flow through it. Due to that, the valve according to the present disclosure may be used for controlling flow of gases and liquids in general, including viscous, pasty liquids with particles in suspension and, specially, with application in the blood flow control, once the valve meets the requirements imposed by the blood tissue.

Figure 4:
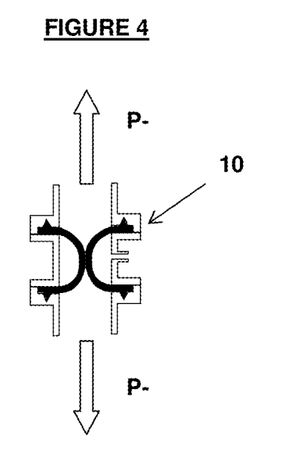
FIG. 4 is a schematic of a membrane valve configured as a bidirectional backflow valve in accordance with embodiments disclosed herein.
Figure 5:
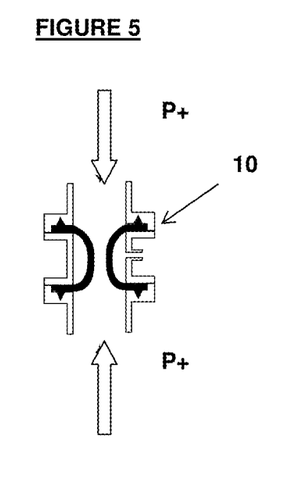
FIG. 5 is a schematic of a membrane valve configured as a bidirectional backflow valve in accordance with embodiments disclosed herein.

Bidirectional Backflow Valve:

The membrane valve (1) in accordance with embodiments disclosed herein, when assembled in circuit in parallel to a main circuit, has the possibility of control by the outlet pressure. During the functional tests of the valve, it was noted that if the control door (10) is kept open for atmospheric pressure, the valve behaves as a bidirectional backflow valve. i.e., the valve opens in both directions if any positive pressure (P+) in one of the sides (5, 6) and closes if applied a negative pressure (P−) in one of the sides (5, 6). This possibility is schematically illustrated by the FIGS. 4 and 5. It is noted that the valve can differ what is negative pressure (P−) than the positive pressure (P+). Also, in this condition, the valve does not function with pressure gradient, but with absolute pressure. For example, if a positive pressure (P+) is applied of one side and the negative (P−) one of the other, there only will be flow if the absolute value (module) of the positive pressure (P+) is higher than the negative pressure (P−) value. Otherwise, there will be not a flow. Therefore, in the described function, the valve will have better performance if the control door (10) is open to the air.

Figure 6:
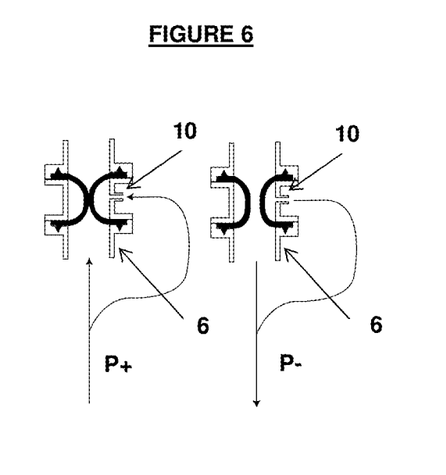
FIG. 6 is a schematic of a membrane valve in accordance with embodiments disclosed herein when positive pressure and negative pressure is applied to the valve inlet.

In another way, as illustrated in the FIG. 6, if the inlet connector (6) is connected to the control door or connector (10), when applying positive pressure (P+) to the valve inlet (6), it closes and, when applying negative pressure (P−) to the valve inlet (6), it opens allowing the flow path, as indicated by the arrows. For example, when applying a pressure P1 to the control door (10), it is defined the valve opening pressure. In this condition, if a pressure P2>P1 is applied to the valve inlet (6), it will open. If P2<P1, the valve remains closed.

Figure 7:
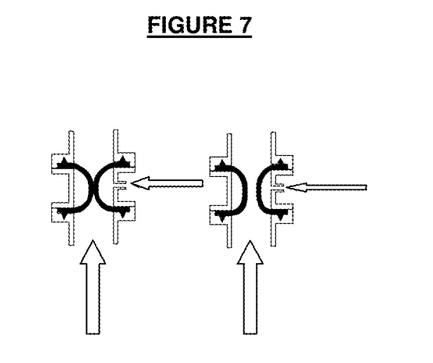
FIG. 7 is a schematic of a membrane valve configured as an adjustable relief valve according to embodiments disclosed herein.

Adjustable Relief Valve:

The membrane valve (1) for controlling flow and pressure relief of the present disclosure may be used as an adjustable relief valve, because always the pressure in its inlet exerts the pressure applied in the control door (10), the valve will open, relieving the pressure. This functionality allows making it as an adjustable relief valve, as illustrated in the FIG. 7.

Figure 8:
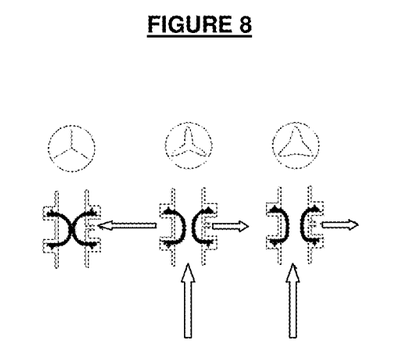
FIG. 8 is a schematic of a membrane valve configured as a flow rate control valve in accordance with embodiments disclosed herein.
Figure 9:
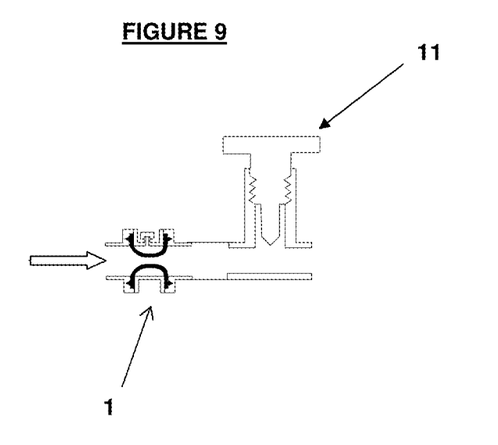
FIG. 9 is a schematic of a membrane valve in accordance with embodiments disclosed herein.

Flow Rate Control Valve:

When applying a positive pressure (P+) or negative (P−) in the control door (10), the valve can be open or closed, so that to interrupt or control the flow rate through the valve. This control may, including, be made at a distance, through the air or fluid, or through an actuator coupled directly to the valve (1), as illustrated in the FIG. 8. This possibility configures the function of flow rate control valve.

Flow Rate Limiting Valve:

When the control door (10) is closed, so that the air inside the enclosure (9) is kept confined, as the flow through the valve increases, the pressure makes the valve to open, compressing the air inside the enclosure (9). Thus, as far as the pressure inside the enclosure (9) increases, the valve opening becomes more difficult. This causes the flow through the valve to be reduced to a value lower than the one that would pass if the valve is totally open. The maximum flow may be set changing the air volume inside the enclosure (9), since it is not a relation of compressor, it is not interior. That is, a maximum valve opening pressure is changed.

In this configuration, the valve of the present disclosure also behaves as a varying resistance, reducing with the pressure increase, since, with low-pressure in the flow line, the valve is almost closed. When the pressure in the line increases, it opens proportionally to the pressure, allowing a higher flow path. Thus, the valve functioning is guided by the equation of the perfect gases:

$$P1 \cdot V1 = P2 \cdot V2$$

wherein:
P1=atmospheric pressure
V1=initial volume inside the air chamber, at atmospheric pressure
P2=final pressure after air compression
V2=final volume after air compression In an example, an embodiment test of the valve according to the present disclosure:
P1=760 mmHg
V1=2.42 ml (closed valve)
V2=1.57 ml (totally open valve)
P2=(760×2.5/0.5)−760=411 mmHg Therefore, for the valve to open fully it is necessary to apply a pressure of about 411 mmHg at its inlet. In this condition, the valve is configured as flow rate limiting.

Also, in tests performed with an exemplary membrane valve model for controlling flow and pressure relief in accordance with embodiments disclosed herein, it was noted that the flow through the valve is directly proportional to the compressed air volume in the enclosure (9) and, therefore, directly proportional to the pressure in its interior.

Pressure Isolator in Hydraulic Circuits:

The membrane valve for controlling flow and pressure relief in accordance with embodiments disclosed herein may also be employed as a pressure isolator, which is commonly used to measure pressures using pressure gauges in hydraulic circuits, without the pressure gauge coming into contact with the liquid contained in the circuit. The pressure isolator transmits the pressure variations from the circuit to the pressure gauge, but isolates the pressure gauge from direct contact with the circuit. For this, the valve (1) according to the present disclosure must have an opening so that the cross-section area is, at least, equal to the cross-section are of the tube to which the valve is connected in order not to create resistance in the line. The internal volume of air moving by the membrane must be enough to cause the total deflection of the pressure gauge reading system. For example, when used with mercury pressure gauges, the folded membrane (7) must be able to move an air volume at least equal to the volume of mercury in the gauge scale. For example, for using a conventional mercury pressure gauge with scale of 300 mmHg, it would be necessary a volume of 20 ml of air between the closed position illustrated in the FIG. 3(a) and the totally open position illustrated in the FIG. 3(f). An advantage of this system is that in the current pressure isolators it is necessary to fill one of the sides of the membrane with liquid to allow reading, but this process is slow and consuming. With the valve of the present disclosure it is not necessary to fill one of the sides with liquid, since it will be assembled in the line and the flow will pass inside it.

Due to the characteristics already described of the valve, it can be applied in blood circuits, notably the CEO circuits. One of the advantages of this same application is that the current pressure isolators are installed laterally, usually in a connector with "Luer-Lock" output, where there is no flow and therefore exposing itself to risks of blood coagulation into the chamber or inside the tube. With the valve, according to the present disclosure, there will be no risk of blood coagulation, since the blood flow will pass through the valve which, as described above, is physiologically shaped.

Figure 10:
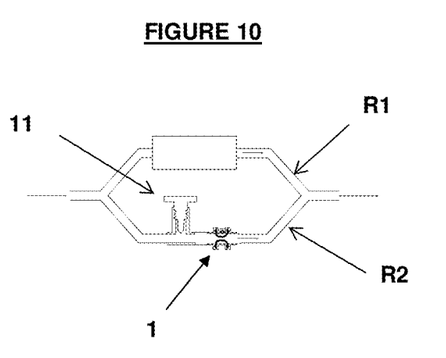
FIG. 10 is a schematic of a membrane valve configured as a ratio controller valve in accordance with embodiments disclosed herein.

Ratio Controller Valve:

The membrane valve for controlling flow and pressure relief in accordance with embodiments disclosed herein may also operate as ratio controller valve. With the control door (10) of the valve closed, it will act such that to compensate resistance variations of a device installed in the branch in parallel, as illustrated in the FIG. 10. In this conception of use, it becomes possible to keep almost constant the flow ratio in both branches (R1, R2), independently of the variations of resistance, flow and pressure in the device in line. As the inlet and outlet of the two branches (R1, R2) are connected, the inlet and outlet pressure are the same. Thus, when the resistance of the device in the parallel line R1 decreases, the total flow increases and the pressure at the outlet will be increased due to increased flow. As a result, the valve will open, reducing also the resistance in its branch R2, keeping the ratio constant. If the resistance of the device in branch R1 in parallel increases, the total flow decreases. As a result, the pressure in the outlet decreases and the valve closes, increasing the resistance in its branch R2 and, consequently, keeping the ratio constant.

Figure 11:
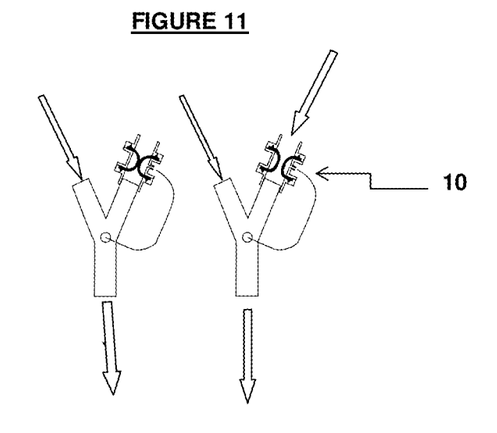
FIG. 11 is a schematic of a membrane valve configured as a vacuum limiting valve in accordance with embodiments disclosed herein.

Vacuum Limiting Valve:

When installed in a negative pressure line, as shown in the FIG. 11, the valve according to the present disclosure may act to stabilize the pressure level in the line. In this function, the control door (10) must be connected to the valve inlet line. In this way, when the vacuum is at low negative pressure, the valve remains closed. When the vacuum pressure increases, the valve opens allowing air to enter. Thus, the air flow in the negative pressure line is within the given limit.

Figure 12:
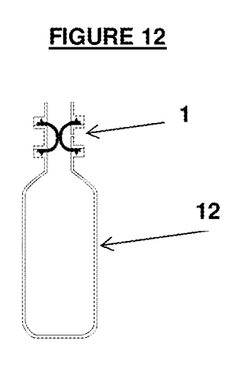
FIG. 12 is a schematic of a membrane valve in accordance with embodiments disclosed herein configured as a self-sealing lid for flasks.

Self-Sealing Lid for Flasks:

The valve of the present disclosure may also be used as a self-sealing lid (1) for flasks (12), as illustrated in the FIG. 12. Thus, in such use, if the flask (12) is kept in the upright position, the valve is closed, preventing its content from contacting the air. If the flask (12) is placed upside down, or compressed, the valve (1) opens, releasing the content thereof. This can be very useful in storing liquids that oxidize when in contact with air or those that evaporate when not properly confined, such as milk, olive oil, fruit juices, alcohol, ether, etc. Another advantage of this use is that to fill the flask (12) it is not necessary to remove the lid, i.e., the valve (1). Simply inject the liquid through the valve (1), wherein, once the liquid is injected, the valve (1) will close automatically. Thus, if the flask is flexible or has a pouch format, for example, and if the container is filled from a state in which the pouch is initially empty and without air inside it, at the end of the filling the pouch will still have no air inside it. Therefore, there is no need to pack the product under vacuum to avoid its contact with the air.

Figure 13:
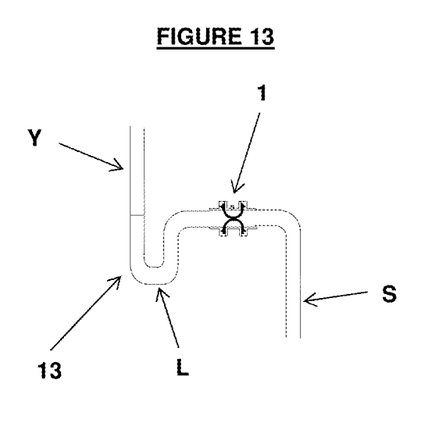
FIG. 13 is a schematic of a membrane valve in accordance with embodiments disclosed herein positioned in an s-pipe.

S-Pipe:

The valve of the present disclosure is assembled in a s-pipe system (13), as illustrated in the FIG. 13, it causes a very interesting effect. The water column (L) after the valve (1) generates a negative pressure which keeps it closed if there is no pressure at its inlet (Y). This avoids the air passage to the outlet (S) and the passage of odors to its inlet (Y). In addition, the valve (1) prevents the liquid present in the inlet (Y) from draining below that level. In this way, there will always be liquid (L) inside the s-pipe tube, which ensures that there will be no odor passing into the inlet (Y) of the valve.

This system may be used in s-pipes of residential sinks and washbasins, or in water tank vents to prevent air from entering the tubing after emptying or when the system is closed for some maintenance.

As seen, the membrane valve for controlling flow and pressure relief in accordance with embodiments disclosed herein may be applied in several situations not being necessary adjustments in its basic structure defined above. Thus, as those skilled in the art will know to search for other applications and uses besides those described above, which will always be inside the scope here described and claimed.

The invention claimed is:

1. A membrane valve for controlling flow and pressure relief, comprising:
   a circular body with terminal sections of greater diameter than a portion of the body between the terminal sections, and having ends for connection in installations; and
   an internally folded membrane, which opens and closes according to the flow and/or the pressure exerted therein, directly or indirectly, locally or remotely,
   wherein the membrane is assembled to form two distinct enclosures, an inner enclosure, as a flow line segment, and an outer enclosure forming an outer space between said membrane and an inner wall of the body, and
   wherein the valve has a form of a sphincter and an action mechanism of a sphincter.

2. The membrane valve for controlling flow and pressure relief, according to claim 1, wherein said outer enclosure comprises a type of air chamber internally to the body of the valve.

3. The membrane valve for controlling flow and pressure relief, according to claim 1, wherein said membrane is tied and fixed in the ends hermetically and avoiding any communication between said enclosures internal to the body.

4. The membrane valve for controlling flow and pressure relief, according to claim 1, wherein the folded membrane comprises internal folds provided in its structure that is made in flexible material.

5. The membrane valve for controlling flow and pressure relief, according to claim 4, further comprising at least three folding or internal folds.

6. The membrane valve for controlling flow and pressure relief, according to claim 1, wherein it is used in blood flow circuits.

7. The membrane valve for controlling flow and pressure relief, according to claim 1, wherein said valve has an outer connector or control door for acting directly in said outer enclosure encompassing axially the enclosure of the membrane.

8. The membrane valve for controlling flow and pressure relief, according to claim 7, wherein said outer enclosure has in its interior a gas or liquid known volume that is fed or removed through an acting element installed in said control door in a way to allow a pneumatic or hydraulic control of coverage or valve closure, either directly or remotely.

9. The membrane valve for controlling flow and pressure relief, according to claim 1, wherein said folded membrane, when in use, may assume any position from totally closed to totally open.

* * * * *